United States Patent [19]
Horn

[11] Patent Number: 5,708,369
[45] Date of Patent: Jan. 13, 1998

[54] CAPACITIVE MEASURING DEVICE

[75] Inventor: Klaus Horn, Braunschweig, Germany

[73] Assignee: Claas Kommanditgesellschaft auf Aktien, Harsewinkel, Germany

[21] Appl. No.: 566,004

[22] Filed: Dec. 1, 1995

[30] Foreign Application Priority Data

Dec. 1, 1994 [DE] Germany ............... 44 42 711.5

[51] Int. Cl.$^6$ .................................................. G01R 27/26
[52] U.S. Cl. ..................... 324/688; 324/687; 324/373; 324/375; 73/304 C
[58] Field of Search ............... 73/304 C; 324/688, 324/663, 689, 690, 687, 373, 375

[56] References Cited

U.S. PATENT DOCUMENTS

| | | | |
|---|---|---|---|
| 3,668,672 | 6/1972 | Parngll | 324/688 |
| 3,798,541 | 3/1974 | Campbell | 324/688 |
| 4,853,614 | 8/1989 | Carver. | |
| 4,899,101 | 2/1990 | Porges. | |
| 5,134,379 | 7/1992 | Maher. | |

FOREIGN PATENT DOCUMENTS

| | | |
|---|---|---|
| 2 151 078 | 10/1971 | Germany. |
| 28 06 153 A1 | 2/1978 | Germany. |
| 31 14 678 A1 | 4/1981 | Germany. |
| 31 33 239 A1 | 8/1981 | Germany. |
| 33 02 736 A1 | 7/1983 | Germany. |
| 30 50 619 C2 | 12/1988 | Germany. |
| 40 22 563 A1 | 2/1990 | Germany. |
| 40 25 400 C1 | 8/1990 | Germany. |
| 40 25 575 A1 | 8/1990 | Germany. |
| 41 05 587 C2 | 2/1991 | Germany. |
| 92 04 374.7 | 3/1992 | Germany. |
| 42 27 922 A1 | 8/1992 | Germany. |
| 43 18 477 A1 | 6/1993 | Germany. |
| 909 505 | 4/1994 | Germany. |
| WO 84/03355 | 8/1984 | WIPO. |
| WO 85/02016 | 5/1985 | WIPO. |

OTHER PUBLICATIONS

Scott et al, Comparison of the Use of Internal and External Electrodes for the Measurement of the Capacitance and Conductance of Fluids in Pipes, J.Phys. E. Sci. Instrum, vol. 18, pp. 587–592, Feb. 1985.

Sami et al, The Use of Capacitance Sensors for Phase Percentage Determination in Multiphase Pipelines, IEEE, vol. 29, No. 1, pp. 24–27, Mar. 1980.

*Primary Examiner*—Ernest F. Karlsen
*Assistant Examiner*—Jose M. Solis
*Attorney, Agent, or Firm*—Browdy and Neimark

[57] ABSTRACT

A capacitive measuring device with a measuring electrode (3) arranged some distance from a counter-electrode (8), a dielectric material for analysis is arranged between the electrodes (3, 8), and a measuring current (IC) is supplied to the measuring electrode (3) and the capacitance-dependent capacitor voltage (UC) is measured and evaluated. The measuring electrode (3) is surrounded by a plurality of guard ring and/or auxiliary electrodes (13, 6N, 6NA) spaced apart therefrom in a staggered arrangement and at least partly covering the side walls (18), and each of which is constantly being corrected via a potential-controlling circuit (17) to the potential of the measuring electrode (3), so as to thereby largely eliminates leakage currents to the guard electrodes (13, 6N, 6NA), in the region of the measurement zone the side wall (18) being virtually completely covered with additional guard electrodes (61–6N; 61A–6NA), divided in a ribbon shape parallel to the measuring electrode (3) or divided in a two-dimensional grid, and each of the guard electrodes is wired to its potential-controlling circuit (17) in a manner that minimizes any flow of current into the guard electrodes (61–6N; 61A–6NA).

22 Claims, 3 Drawing Sheets

CAPACITIVE MEASURING DEVICE

The invention relates to a capacitive measuring device having a measuring capacitor with a measuring electrode arranged spaced apart from a counter-electrode, and with dielectric material for analysis arranged between the said electrodes or continuously being conveyed between them, and there being supplied to the measuring electrode a measuring current that is variable over time and the capacitance-dependent capacitor voltage being measured and evaluated; arranged to the side of a measurement zone provided between the said electrodes, and which if appropriate is a flow duct for the material to be analysed, is at least one side wall arranged so as to delimit the measurement zone, and the measuring electrode being surrounded by a plurality of guard ring and/or auxiliary electrodes spaced apart therefrom in a staggered arrangement and at least partly covering the side walls, and each of which electrode is constantly being corrected via a potential-controlling circuit to the potential of the measuring electrode, so as to thereby largely compensate for leakage currents to the said electrodes.

The use of the capacitive measurement principle has become very important and widespread in metrology applications, notably for the contact-free determination of thicknesses, plate thicknesses, spacings, and filling levels. Its chief advantage lies in the fact that as long as only suitable temperature-resistant materials are used for constructing the sensors there are no fundamental constraints on the latter as regards their ambient temperatures. It is advantageous for the exploitation of the capacitive principle if the structure of the electrical field can be clearly defined in physical terms in the actual measurement volume of the sensor, i.e. for there to be a relationship that can be described in the form of characteristic curves between the sensor's capacitance and the geometrical dimensions of the measurement volume and dielectric properties of the materials that are in the measurement volume.

The basic design of all these capacitive sensors is derived generally from that of a plate capacitor. Where a homogeneous dielectric—such as air—is present between the measuring electrode and the counter-electrode, and we ignore the leakage field capacity, in other words for an idealised plate capacitor, we are left with the simple relationship that its capacitance is equal to the product of the absolute and the relative dielectric constants and the electrode surface divided by the distance between the electrodes.

However, in actual fact at the edges of the electrodes the field-strength distribution is non-homogeneous, and this results in a leakage capacitance which even in the case of a square plate capacitor is additively superimposed on the measuring capacitance of the homogeneous field region in a very non-linear relationship that is difficult to calculate. In its form this leakage field is also extremely dependent on whether in the environment of the measuring capacitor there are additional electrically conductive objects present that exert a vague and complex additional influence on the leakage capacitance, depending on their position and geometrical shape. In order to eliminate the influence—highly undesirable from the metrological standpoint—of these leakage capacitances on the test results, it is standard practice to equip the sensors with additional guard-ring electrodes which are corrected by an impedance transformer by their voltage to within a negligibly small amount to exactly the measuring circuit voltage at the measuring electrode, i.e. one of the field electrodes. The guard-ring electrode normally completely surrounds the measuring electrode along its outer edge and on its reverse face. Its voltage in relation to the potential of the counter-electrode is kept more or less at the potential of the measuring electrode, by an amplifier connected up as an isolation amplifier (buffer) and possessing a very high open-loop gain. The circuitry determines that the measuring-circuit voltage available for further signal processing exactly equals the voltage of the guard-ring electrode, and the fault voltage right as far as the measuring electrode is extremely small compared to the voltage falling across the measuring capacitor.

Therefore no electric field at all develops between the measuring electrode and the guard-ring electrode. It is only between the guard-ring electrode and the counter-electrode that a further leakage field is formed whose size and characteristic, however, do not now exert any influence on the size of the measuring-circuit voltage being developed at the measuring electrode under the effect of a charging current. This measuring-circuit voltage is therefore now exclusively a function of a charging current flowing into the measuring capacitance and is calculated in conventional manner from the time integral of the charging current divided by the measuring capacitance.

The guard-ring principle outlined above presents considerable problems if as a result of the technical scenario the measuring volume in practice extends across a comparatively large measurement cross-section. Such cases for example occur when the task is to determine a mass flow (mass/unit of time) of a material for analysis that is composed of more or less small individual particles (e.g. cereal, chopped green fodder, dust) and conveyed pneumatically or driven by gravity or mass inertia along a delivery duct. This feeder duct is normally at frame potential and is made of a metallic material, with the result that the limits of the delivery cross-section constitute equipotential surfaces at each part of the delivery route. If the conventional guard-ring arrangement is introduced more or less unmodified into such a delivery chute which forms the external boundary of the delivery cross-section and on account of its being earthed also simultaneously constitutes the counter-electrode, this means that a largely non-homogeneous electric field is available to provide the measuring capacitance, for which the simple relationship of the idealised plate capacitor is simply no longer valid. Specifically, this non-homogeneity of the measurement field means that the change in the contribution to the capacitance made by a particle of the delivery flow to the measuring capacitance depends to a great extent on the point of the delivery cross-section at which it passes through the measurement volume. Near to the measuring electrode it will be noticeable as a large capacitance-altering influence, on account of the heavy field concentration. Conversely, at great distances from the measuring electrode the low field density will mean that it only makes a very minor contribution. However, since high-grade mass flow detection means that each mass particle passing through the measurement cross-section ought to provide the same measurement contribution irrespective of where it passes through, so as to enable satisfactory averaging to be performed over all the capacitance-altering contributions, the conventional setups only meet the required standards to a very inexact degree. In spite of the non-homogeneity of the measurement field it is only possible to use the conventional set-up in cases where the delivery flow is able to be concentrated to a comparatively thin and homogeneous layer in relation to the extent of the measurement section, using suitable means (e.g. using centrifugal forces or baffles), with the result that the entire mass flow moves past right alongside the measuring electrode as a densely packed layer.

However, the relationships become completely obscure and highly complex when the mass flow particles are not, as previously assumed, conveyed through the measurement cross-section as individual particles without any physical contact with neighbouring particles, but clump together to form bigger, and in some cases large and coherent, units and thus also to make intimate, electricity-conducting contact with one another. In this case very large field line distortions are to be expected in the immediate vicinity of these clumps, and these will be the more crucial the greater is the electric conductivity of the individual particles. Particularly in the case of very moist organic materials, e.g. chopped green fodder, such resistive conductivity has the effect that not only must the individual particles be comprehended as a dielectric with a real dielectric constant, but that the individual particles also bring about resistive losses in an electric alternating field. Hence a complex dielectric constant is needed to describe the material characteristics of such particles.

As a result of this, when the measuring capacitor is supplied with an alternating current of suitable shape, not only does a pure capacitive reactive current develop between the measuring electrode and the counter-electrode, but also a real, resistive leakage current. It will be immediately apparent that the ratio and size of this reactive and active current is dependent in an extremely complicated fashion on the sizes of the real and the complex dielectric constants, but furthermore on the geometry, the clumping property and the positions of the baked-together clumps of material passing through the measurement cross-section.

In particular, the flow of material with its individual particles cannot usually be prevented from moving along the lateral wall surfaces of the housing and along the lengthened guard-ring electrodes and from coming into intimate electrically conductive contact therewith. This means that to a great extent components from the charging current of the test section are diverted from the delivery flow vertically into surfaces of the housing and guard-ring electrodes, depending on the local potential distribution in the flow cross-section perpendicular to the direction of measurement, or alternatively extra flow components are introduced into the measurement volume from these walls.

From DE 42 27 922 A1 a device is known for measuring a mass flow which is diverted at the exit from an elevator on a delivery chute wall, in particular on a harvesting machine, with the result that it forms a velocity-homogeneous, layered dielectric in a throughput measuring capacitor arranged there. The first capacitor layer of the throughput measuring capacitor is arranged on the mass flow side, and the second capacitor layer is spaced apart from the mass flow. The first capacitor layer is encompassed in a guard electrode which is kept at the same potential as the encompassed capacitor layer by an impedance transformer. The second capacitor layer is formed by a delivery chute wall situated opposite the first capacitor layer and lateral conveyor chute wall areas. The mass flow is conducted through the throughput measuring capacitor in such a way that it forms a layered dielectric with an approximately homogeneous velocity distribution and is passed through a second measuring capacitor which is always quite full. The two capacitances of these capacitors are established using the same measuring device so as to form a capacitance ratio. Measuring the current absolute value of a grain flow in harvesting machines produces considerable advantages when the measured value is used to control and monitor the machine's operation, in particular the rate of advance, the screen drives and the cutting height. Furthermore it enables a harvesting cadastre to be established which forms a basis for year-on-year systematic soil preparation and fertilisation adapted to the particular soil and yield values concerned. In addition to the guard electrode, a further electrode is provided in the said device for the first capacitor layer of the throughput measuring capacitor, and this electrode is adapted to be electrically connected via a changeover switch, either to the guard electrode or to the second capacitor layer. This enables the field distribution to be adapted in each case to the filling level of the capacitor by switching over the second electrode, and enables the electric field line density between the field electrodes to be made more or less homogeneous from case to case.

Furthermore, DE 43 18 447 describes a capacitive measuring device of the type outlined at the start, having two parallel field electrodes with two guard electrode layers which surround the first field electrode at staggered distances apart, the first of which is supplied with the potential of the first field electrode via an impedance converter and the second is supplied via a further impedance converter with an intermediate potential somewhere between that of the first and second field electrode. A compensating circuit controls the intermediate potential in such a way that any leakage currents that may be produced by a coating of moisture on the compensating electrodes are discharged to the second field electrode and a leakage current cannot disturb the measuring current at the first field electrode, thereby allowing uninsulated electrodes to be used that are resistant to wear. However, the capacitive measurement field only has the necessary homogeneity over a sub-region, which means that homogenisation and layering of the material for analysis has to be carried out.

SUMMARY OF THE INVENTION

It is the object of this invention to improve upon the device outlined at the beginning so that there is always as complete a homogeneous field distribution as possible between the field electrodes, irrespective of how the material is distributed in the measurement zone and of the reactive and active components of the material and of unsystematic wall current flows.

The solution consists in the fact that in the region of the measurement zone the side wall is virtually completely covered by additional auxiliary electrodes, divided in a ribbon shape parallel to the measuring electrode or divided in a two-dimensional grid, and each of the auxiliary electrodes is wired to its potential-controlling circuit so as to minimise any flow of current into the auxiliary electrodes.

BRIEF DESCRIPTION OF THE DRAWINGS

FIG. 1 depicts a cross-section taken through a mass flow channel or duct. The entire expanse of the side walls (18) of the flow duct are covered in the measurement direction with ribbon-shaped auxiliary electrodes (61–6N) which consist of an abrasion-resistant, metal conductor, e.g. special steel plate, and are preferably cemented onto the side walls (18) by an electrically insulating adhesive (2). These ribbon-shaped electrodes (61–6N) are electrically insulated from one another by thin insulating sections, preferably made from the adhesive material (2), and they run parallel to the axis of the flow duct and extend for a length that is preferably slightly greater than the expanse of the measuring electrode (3) with the guard-ring electrode (13) towards the centre axis of the flow duct (1).

Each of these auxiliary electrodes (61–6N) is linked to an electronic potential-controlling circuit (17), whose job it is to adjust the potential of the associated auxiliary electrode in such a way that on balance the latter does not receive any current from the measurement volume or emit any thereto. If the width of this auxiliary electrode (61–6N) is very small, i.e. if the number (N) of auxiliary electrodes is increased for given dimensions of the flow duct, the effect of this measure is that irrespective of the form and make-up of the electrical field in the measurement volume as a consequence of material particles (7) or clumps (41–45) thereof distributed irregularly over the measurement cross-section, no transverse flows perpendicular to the direction in which the material is flowing and perpendicular to the direct connection between the measuring electrode and the counter-electrode (3, 8) are exchanged at the side walls (18) and the auxiliary electrodes (61–6N). Thus the direct consequence is that despite all conceivable field distortions on balance only flow components are able to flow between the measuring electrode and the counter-electrode (3, 8), which means that even where the material passing through is very unevenly distributed in particles or clumps the resulting electrical field is quasi-homogeneous.

In accordance with the invention an additional improvement of this side wall potential control may also be obtained by further dividing each of the auxiliary electrodes (61–6N) initially assumed to be continuously ribbon-shaped into M individual electrodes in the direction of flow. In accordance with the invention each of these M individual auxiliary electrodes is then equipped with a similar electronic potential-controlling circuit (17). The effect of this measure is that even in the case of field distributions, which as a result of non-homogeneous material distribution in the measurement volume is variable in the direction of material flow, the desired field homogenisation is also optimised in those peripheral zones in the direction between the measuring electrode and the counter-electrode. Overall on the electronics side one now arrives at a matrix-type arrangement of many identically constructed individual potential-controlling circuits, with the overall number n=N·M, which if today's microelectronic production processes and available options are utilised can be manufactured without any difficulty as an integrated circuit in a very small space and with low set-up costs.

Figure 1:
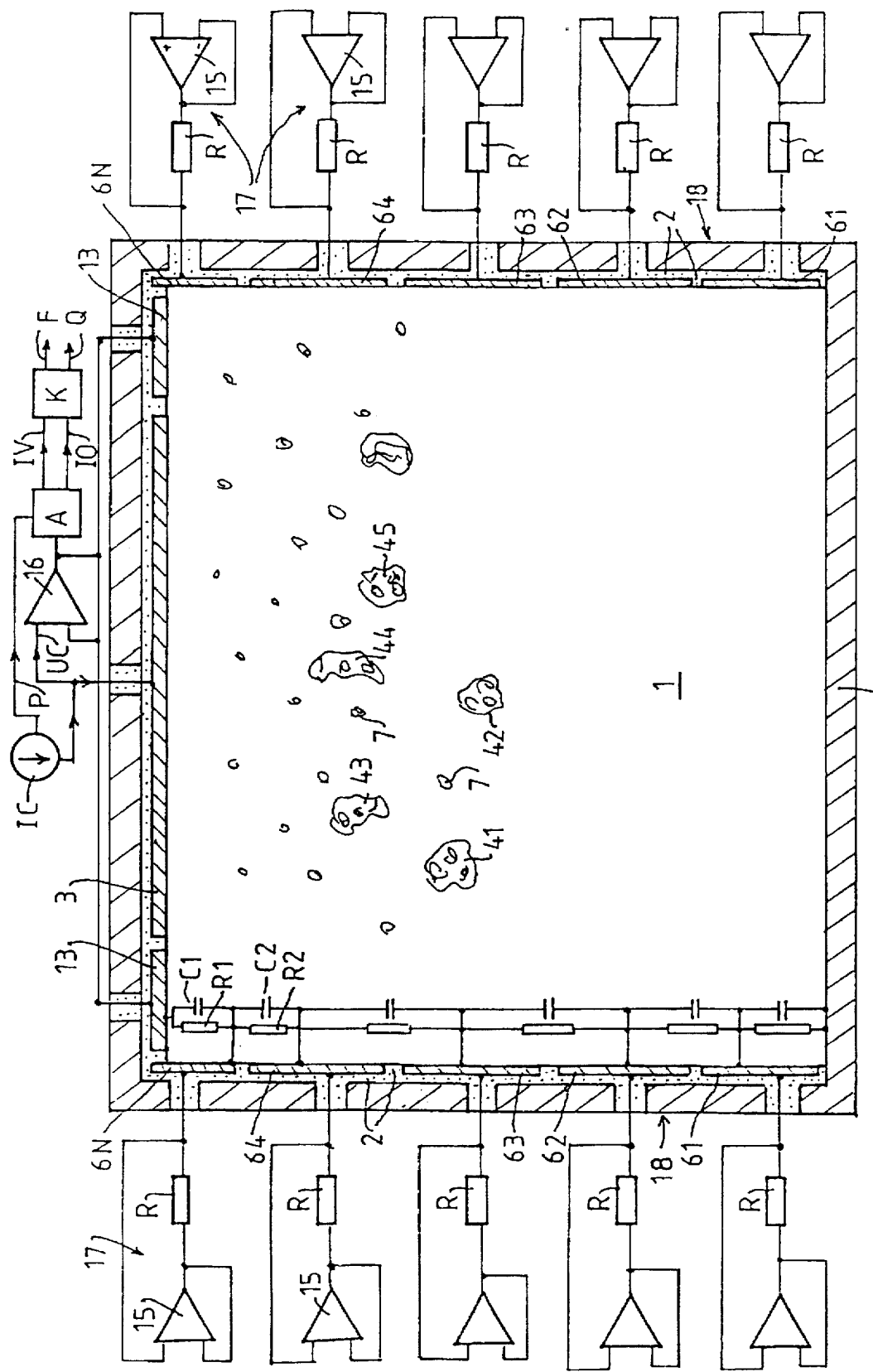
FIG. 1 shows a cross-section through a first type of measuring set-up.

The layout of the potential-controlling circuits (17) according to the invention advantageously follows the wiring diagram reproduced in FIG. 1. The operational amplifiers (15) have a very high voltage open-loop gain, advantageously higher than a million. The negative feedback resistance (R) is in each case an ohmic resistance, not necessarily control-independent, which brings about negative feedback of the control circuit. The auxiliary electrodes (61–6N) are arranged as wall electrodes; their potential is controlled by the potential-controlling circuits (17) in such a way that the currents (Ia) in and out of these electrodes are minimised. On the right-hand side of the auxiliary electrode (6N), and representative of all the auxiliary electrodes, is shown a simulation of the material for analysis (7, 41–45), an imperfect dielectric, of which the loss resistances (R1, R2) result individually at the site of the auxiliary electrode (6N) under the effect of the momentary ohmic losses of the material to be analysed. The sub-capacitances (C1, C2) are predetermined by this very material to be analysed under these conditions. These four impedances are all supplied by the capacitor voltage (UC). Thus the potential (R1, C1; R2, C2) of the auxiliary electrodes (6N) is in each case unequivocally determined from these four impedances using the imperfect voltage divider, just so long as the current (Ia) flowing in the auxiliary electrode (6N) is kept very tiny. Even where the wall electrode potential is comparatively large, in the case of very large open-loop gains and a large negative feedback resistance (R) (e.g. at least 1M Ohm), in each case the current (Ia) into the auxiliary electrode can be kept so small that it no longer has any effect whatever on the potential distribution preset by the mass flow (material for analysis) in the measurement volume. Even where non-stationary conditions prevail, i.e. if the capacitor voltage (UC) is a sinusoidal or saw-toothed alternating voltage, the potential-controlling circuit will operate satisfactorily, except that the wall current (Ia) is no longer in phase with the capacitor voltage (UC).

Another advantage of the circuit is the fact that even if the potential increases from, say, 10 volts and a gain factor of a million and a negative feedback resistance of 1 MOhm, the grid-driving power to be supplied by the operational amplifier (15) will only assume values of 0.1 microwatt. This means that even in the case of the preferred use of auxiliary electrode matrices, despite a fairly large number of auxiliary electrodes the power requirement remains within the range of a few milliwatts and in this way it is possible to achieve a high integration density for a microelectronic circuit design.

Figure 2:
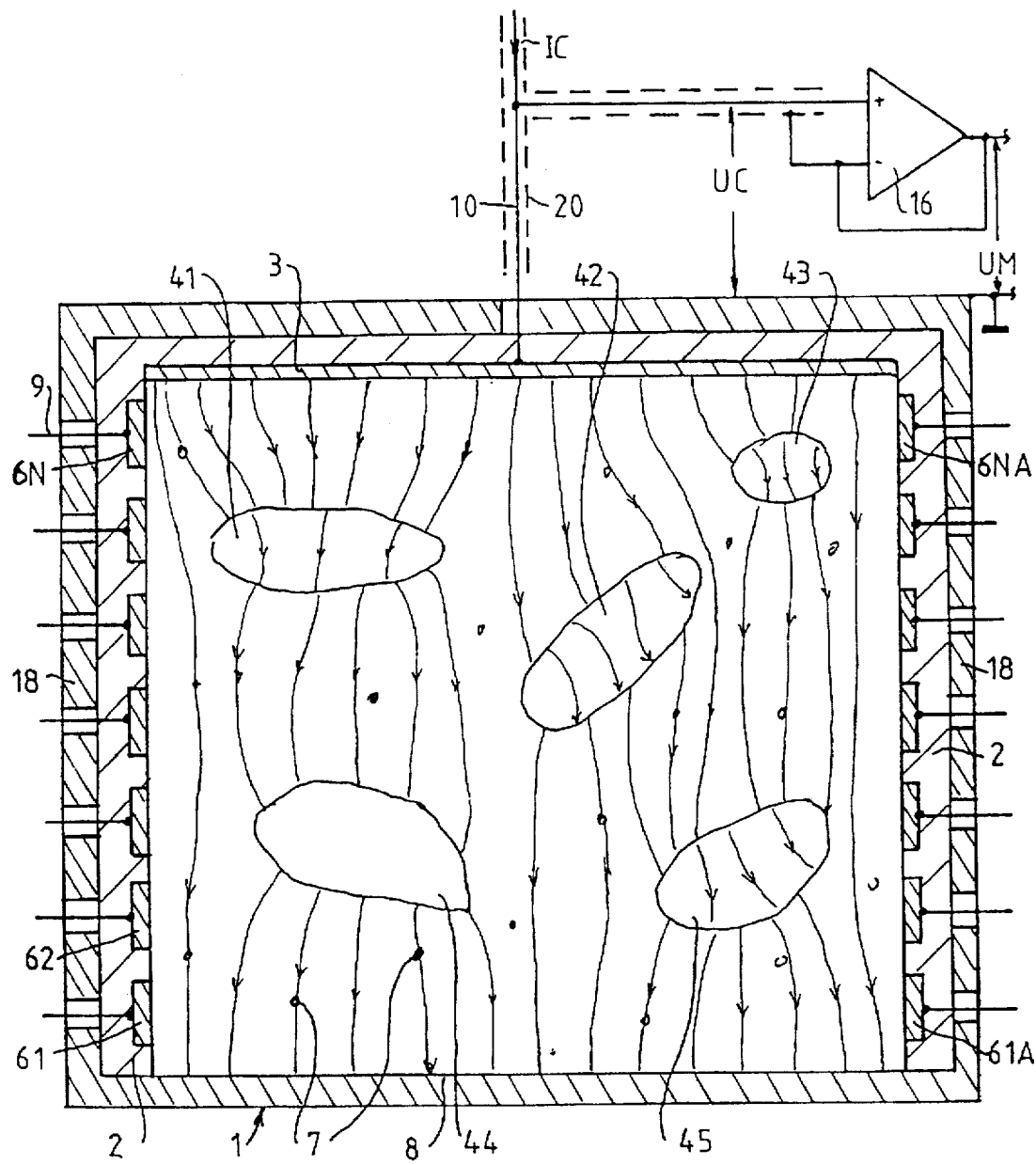
FIG. 2 shows a cross-section through a second type of measuring set-up.

FIG. 2 depicts a cross-section taken through a flow channel, in which a plurality of clump-shaped accumulations (41–45) of material for analysis move through the measurement volume in a random spatial arrangement, thus representing how the measures in accordance with the invention impact upon the field distribution. The electronic potential-controlling circuits (17), which are not reproduced here individually but have already been described above, automatically bring all the wall electrodes (61–6N) and their connections (9) to a potential such that no lateral capacitive or ohmic currents (Ia) are discharged via these auxiliary electrodes. Because this measure means that in even in the immediate vicinity of the measuring electrode (3) it is not possible for any displacement currents to be discharged laterally (the potential of the auxiliary electrodes (61–6N) being corrected by their associated electronic control systems to more or less the potential of the measuring electrode (3)), for practical purposes these auxiliary electrodes assume the function of the previous guard-ring electrode (13), which in FIG. 1 is still shown as separate. This has the advantage that the measuring electrode (3) now runs the entire width of the delivery duct's cross-section, and thus the full measurement cross-section is included in the material flow measurement down to the very smallest angle.

In FIG. 2 the qualitative design of the field line characteristic in the measurement cross-section assumes that the clumped material components (41–45) all have a large relative dielectric constant compared to 1, with the result that in its interior a much smaller field line density prevails than in the surrounding air space. It will be recognised that compared to a strictly homogeneous field distribution, considerable field distortions will be caused if clumps of material bring these disturbances into the measurement volume. But since the foregoing wall potential control means that no displacement currents at all enter or leave the two side walls (18) covered with the auxiliary electrodes (61–6N), in other words nothing is lost or added, the entire displacement current emerging from the measuring electrode (3) arrives at full strength at the opposing counter-electrode (8), which to make matters more straightforward consists directly of the earthed casing wall material of the feeder duct. From this qualitative representation it will also readily be immediately obvious that each volume element of the entire measurement volume is in this way assured of approximately equal weighting in its effects on the overall displacement current flow (IC) passing through the measurement volume. Quite analogous conditions also result when the clumps of material are positioned not only as an ideal dielectric, but with a certain internal ohmic conductivity, which leads to ohmic loss currents also flowing within these clumps of material (41-45), in addition to the displacement currents depicted in FIG. 2. These loss currents ensure that the resulting field lines there feature more or less major phase shifts as compared to the purely capacitive displacement currents in the air space. These conditions can also be taken into account by setting a complex dielectric constant for the material. In any case the aforesaid loss currents in the clumps of material (41-45) ensure that compared to the measurement current (IC), namely the supplying alternating current, the measuring voltage (UC) at the measuring electrode (3) incorporates a phase shift that is functionally dependent on these losses.

By phase-selective signal processing of the measurement voltage (UM) based on the phase of the measurement current (IC), the said measurement voltage (UM) occurring at the output of the measuring impedance converter (16) and largely corresponding to the capacitor voltage (UC), it is therefore possible to break down the reactive and active components of the said measuring voltage (UM) into its proportionate components and thereby draw conclusions as to the composition of the material, e.g. from a dry mass with purely dielectric conduction and a moist component with primarily ohmic conduction.

The operational amplifier (16) is used for impedance conversion and, as FIG. 1 shows, is wired as an isolation amplifier, or buffer. Consequently, apart from the very small, virtually negligible input voltage of the amplifier (16) the signal voltage (UM) is always exactly the same as the capacitor voltage (UC) falling across the measuring electrode (3). In order to render the effect of the cable linking the measuring electrode (3) and the positive input of the amplifier (16) insensitive to capacitive influences from conductive objects nearby (body effect), in conventional manner this link is surrounded by a screen (20) which is connected to the negative input of the amplifier (16) and ensures that between the screen (20) and the measuring line (10) only ever the afore-described negligible voltage drop occurs at the input of the amplifier (16). In case of need it may also be advantageous to connect the auxiliary electrodes (6N) adjacent to the measuring electrode (3) direct to the negative input of the measurement amplifier (16) rather than to their own potential electronic control system (17); in the same manner these auxiliary electrodes (6N) then assume the function of the guard-ring electrode (13) still positioned in the plane of the measuring electrode (3), though without restricting the measurement volume registered by the measuring electrode (3).

However, the functioning of the wall potential control system by means of finely divided auxiliary electrodes (61-6N) only operates satisfactorily when there is respective satisfactory electrical insulation between two neighbouring auxiliary electrodes. If this is not the case, then between the two neighbouring electrodes a compensating current will flow that is proportional to the potential difference between the two auxiliary electrodes, but inversely proportional to the intervening insulation resistance. Where such insulation fault currents occur, however, this renders the stated potential control circuit (17) incapable of properly fulfilling its function.

In practical operation insulation defects of this type cannot, however, be safely prevented at many locations and sites of use. In the first place it is possible for moisture in the form of a film to be deposited on the entirety of the walls of the conveying duct and thus also on the side walls (18) having the auxiliary electrodes (61-6N). As a rule such deposits of moisture have an equipotential bonding value that is far from neutral and hence to a greater or lesser extent are electrolytically conductive. Insulation defects that may in some cases be much more serious could occur if small portions break away from the material being conveyed and become deposited and baked onto the walls. The effect of this type of covering layer too over the auxiliary electrodes would be directly comparable with that of moist precipitation, for it must generally be assumed that the materials being conveyed likewise possess the ability to conduct electricity.

Figure 3:
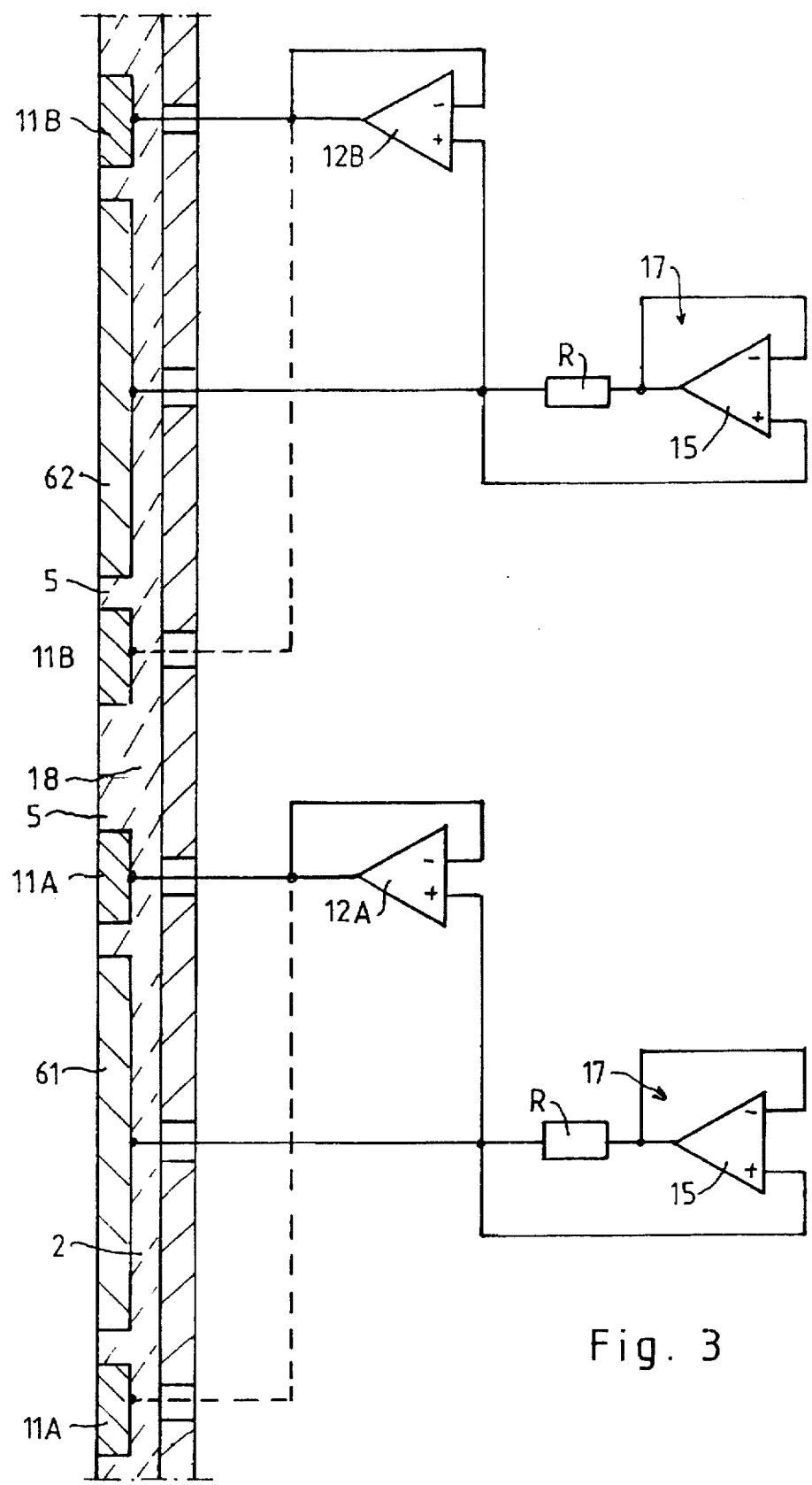
FIG. 3 shows a cross-section through a third type of measuring set-up.

In order to eliminate such disturbances and weaknesses, in accordance with the invention and as seen in FIG. 3 each auxiliary electrode (61, 62) is enclosed in a ring by a guard electrode (11A, 11B) which is insulated from it. By means of an operational amplifier wired as a guard buffer (12A, 12B), each of these guard electrodes (11A, 11B) is constantly being corrected virtually instantly to the potential to which the imprisoned auxiliary electrode (61, 62) is controlled by its associated potential-controlling circuit (17). On account of the minimal potential difference between the enclosed auxiliary electrode and the guard electrode which surrounds it, which is of the order of 1-2 μV, even in the case of a relatively low-ohmic bridging of the insulating gap between the guard electrode (11A) and the auxiliary electrode (61) no compensating current is able to flow through a conductive coating, with the result that the coating causes no further difficulty.

However, as will be apparent in FIG. 3, in the case of the arrangement of auxiliary and guard electrodes according to the invention a respective two guard electrodes (11A) and (11B) kept at different potentials are arranged alongside one another and separated merely by a narrow isolating member (5). If a deposit of moisture or material produces an electrically conductive bridge here, a compensating current depending on the potential-difference will then flow between the neighbouring guard electrodes (11A) and (11B) and the variable that is the disruptive ohmic conductance of the bridging coating section. This compensating current must be supplied proportionally by the associated guard potential buffers (12A, 12B); it has virtually no influence on the field distribution and geometric characteristic of the field lines of the displacement currents in the measurement volume.

With the help of these measures according to the invention it is therefore also possible under all the adverse conditions outlined above to achieve the desired field homogeneity in the measurement volume, even when very unfavourable operating conditions cause deposits of moisture or material to form on the potential-controlled side wall surfaces (18).

Thus in accordance with the invention the characteristic is controlled in respect of the electrostatic and the electrical flow pattern in the measurement volume of a seemingly largely plane plate capacitor consisting of a measuring electrode (3) installed with insulation, and a diametrically opposed counter-electrode (8) of roughly equal size which may be earthed and part of a metal casing which surrounds the measurement volume in its entirety, such that all displacement currents coming from the measuring electrode (3) and conduction currents, irrespective of field distortions due to material (7, 14) occupying the measurement volume, discharge fully and exclusively into the counter-electrode (8) and are not in part discharged into the side walls (18) of the surrounding casing or from there additionally flow to the components, by virtue of the side walls (18) being covered by a large number N of auxiliary electrodes (61–6N; 61A–6NA) divided at right angles to the direction of the field, the said auxiliary electrodes being electrically insulated from one another and from the side wall (18) and in each case being wired to a potential-controlling circuit in a manner minimising the flow of current into the auxiliary electrodes.

In one preferred embodiment each of the auxiliary electrodes (61–6N) is in the shape of a ribbon which runs in the direction of the axis of the casing surrounding the measurement volume, and which has a length at least the same or slightly greater than the length exhibited by the measuring electrode (3) together with a guard-ring electrode (13) which may, if appropriate, surround the measuring electrode (3) in the said direction.

In another embodiment these ribbon-shaped auxiliary electrodes are each divided once more into a total of M subsidiary auxiliary electrodes, which are electrically insulated from one another. In this manner there is on each wall surface (18) a matrix-like arrangement of in all N·M subsidiary auxiliary electrodes. Each of these subsidiary auxiliary electrodes has its own electrode lead wire. Connected to each electrode lead wire is an electronic control circuit (17) which regulates the potential of the associated auxiliary electrode exactly to the potential that the field in the measurement volume would adopt, given an identical covering of material, if the side walls (18) were composed of an idealised non-conductive, yet not statically charging material. This idealised state is characterised by the fact that no displacement current components whatsoever enter or exit from the measurement volume into the side walls (18). However, in accordance with the invention it is precisely this state that is generated by the electronic potential-controlling circuits respectively linked to the auxiliary electrodes, the said circuits being designed so that no current whatsoever is transported between the respective connected auxiliary electrode and the measurement volume.

In another practical embodiment, the electrical interference produced under unfavourable application conditions due to layers of dielectrically or ohmically conductive material or moisture being deposited on the side walls having the auxiliary electrodes is prevented by virtue of the fact that each individual auxiliary electrode is surrounded by its own guard electrode (11A, 11B) and its potential corrected without delay to the potential of the associated auxiliary electrode with the help of an operational amplifier wired as a buffer (12A, 12B). These buffers (12A, 12B) supply the ohmic or dielectric compensating currents which flow between two neighbouring guard electrodes (11A, 11B) on account of the potential difference.

In accordance with the invention, the potential-controlling circuits (17) are produced together with the buffers (12A, 12B) for the guard electrodes (11A, 11B) for all the auxiliary electrodes (61–6N) in a common microelectronic manufacturing process on one substrate and made in the form of a microelectronic chip.

The—otherwise complex—mechanical production of the auxiliary electrodes (61–6N) and, if appropriate, of the associated guard electrodes (11A, 11B) is advantageously carried out in a photolithographic etching process in which the starting material used is a highly abrasion-resistant insulating material, e.g. glass-fibre polyester, which is coated with a sufficiently thick metal foil likewise of highly abrasion-resistant material, e.g. high-grade steel. In order to obtain an optimally smooth surface facing the measurement volume once the auxiliary and guard electrodes have been etched out, it is preferable to finally push the whole electrode assembly under pressure into the backing material by the application of heat while the backing material has not yet completely hardened, until the gaps between the electrodes are completely filled with the insulating backing material and form flush insulating lands (5).

In advantageous manner the use of a signal evaluating circuit (A) (see FIG. 1) between the capacitive displacement current (IV) and the ohmic leakage current (IO) through the measurement volume, which circuit processes the measuring voltage (UC) in phase-selective manner based on the phase (P) of the measurement current (IC), allows the size of the capacitive and ohmic components of the measurement current through the measurement volume to be separately established. A correlation (K) is used to determine from this the dry proportion (Q) and the water content (F) of the medium in the measurement volume, or else ratios of other components of a two-substance mixture having different electrical component characteristics and the overall content of the substance are determined in this way.

The crucial advantage over conventional devices is the fact that the measurement result is totally independent of how the material is arranged in the measurement volume. Moreover, the two-phase assessment now made possible for the first time by eliminating the effects of moisture on the wall zone does away with the need to use a comparative measuring capacitor for separately determining the moisture content, as was always used with conventional devices.

I claim:

1. In a capacitive measuring device for dielectric material to be analyzed, the device including
    a measuring electrode (3) a distance from a counter-electrode (8) with the material disposed therebetween,
    current means for supplying to the measuring electrode a time-variable measuring current (IC), and
    measuring means for measuring and evaluating a capacitance-dependent capacitor voltage (UC);
    the improvement comprising:
        a plurality of auxiliary electrodes (6N, 6NA) disposed between the measuring electrode (3) and the counter-electrode (8) on two sides of the material, the auxiliary electrodes being disposed in a staggered formation;
        each of the auxiliary electrodes being coupled to a respective potential-controlling circuit (17) including minimal-current-flow means for compensating for leakage currents into or out of each of the auxiliary electrodes.

2. The improvement according to claim 1, characterised in that each of the potential-controlling circuits (17) comprises a potential-controlling amplifier (15) whose output is linked via a high-resistance degenerative resistor (R) to the auxiliary electrode (6N) and whose two inputs are respectively connected to one or other of the connections of the degenerative resistor (R).

3. The improvement according to claim 2, characterised in that the potential-controlling amplifier (15) has at least a gain of one million and the degenerative resistor (R) features at least one 1 MOhm.

4. The improvement according to claim 1, characterised in that each of the auxiliary electrodes (61–6N; 61A–6NA) is surrounded by its own narrow guard electrode (11A, 11B) which is supplied via a guard buffer (12A, 12B) with the potential of the associated auxiliary electrode (61–6N; 61A–6NA) at relatively low resistance.

5. The improvement according to claim 4, characterised in that the guard buffer (12A, 12B) is a high-gain impedance transformer with negative feedback, whose input is connected to the associated auxiliary electrode (61–6N; 61A–6NA).

6. The improvement according to claim 1, characterised in that the plurality of the potential-controlling circuits (17), are integrated in a monolithic circuit.

7. The improvement according to claim 6, characterised in that only the outputs of the potential-controlling circuits (17) pass out of the monolithic circuit.

8. The improvement according to claim 1, characterised in that a guard-ring electrode (13) is arranged so as to surround the measuring electrode (3) in one plane with the latter.

9. The improvement according to claim 1, comprising an abrasion-resistant, highly insulating plastic or adhesive (2) terminating flush with a measurement zone bordered by the measuring electrode, the counter-electrode, and the auxiliary electrodes, and comprising insulating lands (5) and connections (9) through a shield connected to the counter-electrode (8).

10. The improvement according to claim 9, characterised in that the auxiliary electrodes (61–6N; 61A–6NA) and the guard electrodes (12A, 12B) are made of high-quality steel plate.

11. The improvement according to claim 9, characterised in that the plastic or adhesive (2) and the insulating lands (5) are made from glass-fibre polyester.

12. The improvement according to claim 1, characterised in that the capacitor voltage (UC) is evaluated for phase in an evaluating device (A) in relation to the time varying measurement current (IC) and in this way the sizes of the displacement current (IV) and of the ohmic leakage current (IO) are established, the variables (IV, IO) thereby obtained being assigned to conventional material characteristics (F) and quantities of material (Q) in a correlator (K).

13. The improvement according to claim 12, characterised in that the material characteristic (F) established in the correlator (K) is the moisture content of the material, in particular of harvested material.

14. The improvement according to claim 6, wherein only outputs of the potential-controlling circuits (17) and the respectively associated guard buffers pass out of the monolithic circuit.

15. The improvement according to claim 1, wherein the auxiliary electrodes are substantially perpendicular to the measuring electrode.

16. The improvement according to claim 1, wherein the auxiliary electrodes (6N, 6NA) are disposed on side walls of a duct and wherein the auxiliary electrodes substantially cover the side walls.

17. The improvement according to claim 16, wherein the auxiliary electrodes (6N, 6NA) comprise parallel strips parallel to the duct.

18. The improvement according to claim 16, wherein the auxiliary electrodes (6N, 6NA) comprise a two-dimensional grid.

19. The improvement according to claim 18, wherein the material is continuously conveyed along the duct.

20. The improvement according to claim 4, comprising an abrasion-resistant, highly insulating plastic or adhesive (2) terminating flush with a measurement zone bordered by the measuring electrode, the counter-electrode, the auxiliary electrodes, and the guard buffers, and comprising insulating lands (5) and connections (9) through a shield connected to the counter-electrode (8).

21. The improvement according to claim 4, wherein the potential-controlling circuits (17) and the guard buffers (12A, 12B) are integrated into a monolithic circuit.

22. The improvement according to claim 14, wherein the auxiliary electrodes and the guard electrodes are made of high-quality steel plates.

* * * * *